United States Patent [19]

Rainer

[11] Patent Number: 4,890,916

[45] Date of Patent: Jan. 2, 1990

[54] ILLUMINATOR FOR A REFRACTOMETER

[76] Inventor: E. H. Rainer, 3401 Virginia Rd., Cleveland, Ohio 44122

[21] Appl. No.: 241,321

[22] Filed: Sep. 7, 1988

[51] Int. Cl.[4] .......................................... G01N 21/41
[52] U.S. Cl. .................................................. 356/135
[58] Field of Search ................ 356/128, 135, 136, 137

[56] References Cited

U.S. PATENT DOCUMENTS

| 2,601,128 | 6/1952 | Rosenthal et al. | 356/137 |
| 4,243,321 | 1/1981 | Okuda et al. | 356/135 |
| 4,650,323 | 3/1987 | Nakagawa | 356/135 |

Primary Examiner—F. L. Evans
Attorney, Agent, or Firm—Watts, Hoffmann, Fisher & Heinke

[57] ABSTRACT

An illuminator for use in a hand-held refractometer used for measuring the composition of substances. The refractometer comprising a hand-held body housing a prism and measuring assembly with a prism surface for supporting the substance to be measured, wherein the illuminator illuminates the substance to be measured. The illuminator comprises a light source positioned on or about the prism surface supporting a substance to be measured, and a power source for operating the light source. An operating assembly is also provided for manually activating the light source by selectively bringing it into communication with the power source. The light source, power source, and operating assembly form an illuminator assembly which supports the light source in a position on or about a prism surface in order to illuminate a substance to be measured at an angle with respect to the prism surface.

9 Claims, 2 Drawing Sheets

ILLUMINATOR FOR A REFRACTOMETER

TECHNICAL FIELD

This invention relates to an illuminator for a measuring device and more particularly to an illuminator for a hand-held refractometer.

BACKGROUND ART

Refractometers are commonly used in industry to measure the index of refraction in chemical compositions. Once determined, the refraction index of a substance can be used to measure and thus control the concentration of elements within the substance.

Temperature compensated hand-held refractometers are also commonly used to measure refraction indices of vehicle fluids at various temperatures. In industries which maintain a fleet of vehicles, such as buses, trucks or planes, temperature compensated refractometers are able to provide a convenient means for frequently testing the concentration levels of crucial vehicle fluids, such as glycol based anti-freezes and batteries.

Similarly in the chemical, soft-drink or juice industries, it is often necessary to determine the level of sugar in the fluids manufactured. Temperature compensated refractometers having Brix scales for determining percent sugar levels are convenient for such testing.

Refractometer devices previously available are disclosed, for example, in U.S. Pat. Nos. 3,267,795 and 3,329,060. In such prior art refractometers, the testing of fluids is accomplished by removing samples, applying them to the refractometer and reading the results from an internal reticle scale or digital readout. The refractometer is able to compensate for the temperature and concentration of the fluid being measured, and converts the refraction index directly to a protection rating, such as the minimum temperature protection provided by an anti-freeze sample, or the percentage of solids or mixture content in a substance. No further calculation or conversion of the reading is required.

Measuring the concentration or protection levels of manufactured fluids enables rapid determinations to be made as to whether the levels are acceptable or require adjustment. The simplicity of the test procedure also enables measurements to be made by manufacturing or maintenance personnel without special training.

One disadvantage of these prior art devices has been that measurements can only be made in the light, since refraction index measurements are of changes in the light path passing through the substance to be tested. Thus, a light source is required for performing the measurements. Operators of refractometers taking measurements in unlighted or dimly lighted areas during the night have been inconvenienced by having either to move to a well lighted area or to carry an external light source.

DISCLOSURE OF THE INVENTION

The present invention provides a novel illuminator for a refractometer having a hand-held body housing a prism and measurement assembly with a prism surface for supporting a liquid substance to be measured, wherein the illuminator includes a light source on or about the prism assembly, a power source for operating the light source, and an operating assembly for manually activating the light source. The light source, power source, and operating assembly form an illuminator assembly. The illuminator assembly supports the light source such that it is positioned to reflect on or about the prism surface during measurement of the fluid substance.

In accordance with one preferred form of the invention, the illuminator is mounted externally on the refractometer body, with the illuminator assembly housed in a cover plate of the refractometer. The cover plate is preferably of a light transmitting material, and includes an engagement surface for engaging the fluid substance measured on the prism surface, leg portions removably hinged to the refractometer body, and an internal cavity for housing the illuminator assembly.

In the preferred form, the illuminator assembly supports the light source in a position on or about the prism surface so that during measurement of the fluid substance the light source illuminates the fluid at an angle with respect to the prism surface.

The power source operating the light source, and operating assembly manually activating the light source are also housed within the cover plate in the preferred form of the invention. The power source comprises a miniature battery. The operating assembly comprises a cap covering a finger operated switch for engagement with the battery, and a resistor interconnected between the battery and the light source for limiting current flow to the light source.

The operating assembly is operated as necessary by providing finger pressure to the cap, thereby engaging the switch to contact the battery, complete the circuit and activate the light source. The light source is deactivated once pressure is removed from the cap disengaging the switch from the battery to break the circuit.

Other features and advantages of the present invention will become apparent from the following detailed description of a preferred embodiment made with reference to the accompanying drawings forming part of the specification.

BEST MODE FOR CARRYING OUT THE INVENTION

Figure 1:
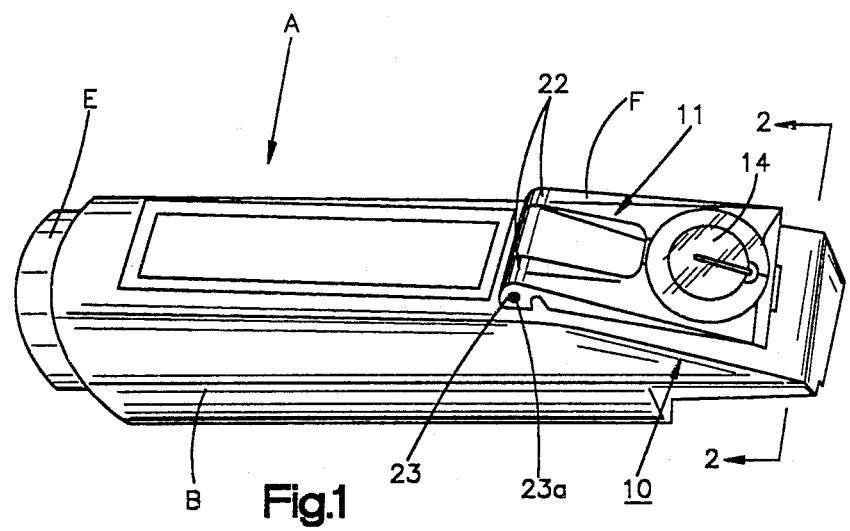
FIG. 1 is a perspective view of an illuminator constructed in accordance with the present invention mounted on a hand-held refractometer.
Figure 2:
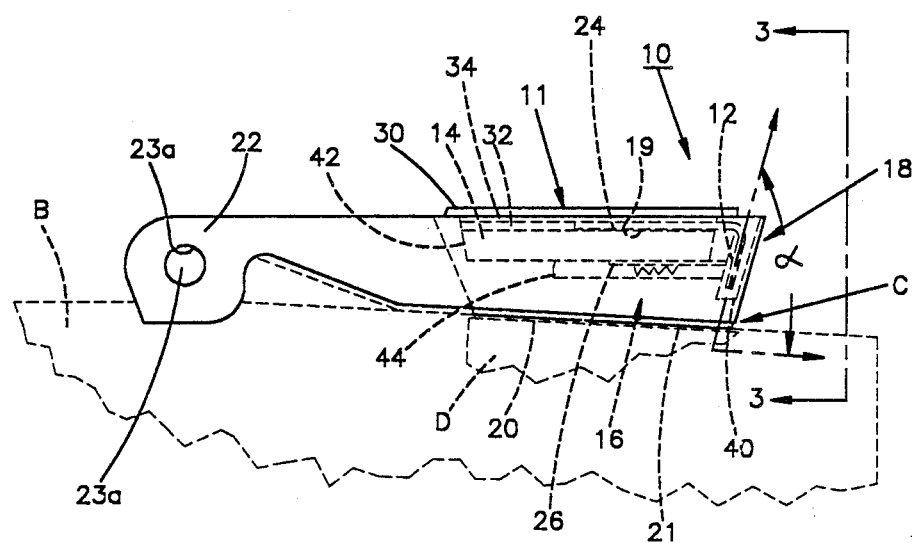
FIG. 2 is an enlarged side view of the illuminator of the present invention taken along the line 2—2 of FIG. 1.

An illuminator 10 constructed in accordance with the present invention is illustrated in FIGS. 1 and 2 of the drawings together with a hand-held refractometer A, having a prism assembly for measuring the composition of fluid substances. The illuminator 10 is housed within a removable cover plate 11, and includes a light source 12 positioned on or about the refractometer prism assembly, a power source 14 for operating the light source, an operating assembly 16 for manually activating the light source 12 by selectively bringing it into communication with the power source 14, and an illuminator assembly 18 supporting the light source 12 at a position on or about a fluid substance C to illuminate the substance at an angle, generally referred for example at character α, with respect to the prism assembly.

The refractometer comprises a hand-held body B housing a prism assembly, in part represented by the reference character D, a measuring assembly (not illustrated), and an eye piece E. The prism assembly B includes a main prism surface 20 supporting the fluid substance C to be measured which engages the cover plate 11. U.S. Pat. Nos. 3,267,795 and 3,329,060 which discuss and detail the internal prism assembly, measuring assembly, including use of the reticle scale, and operations of hand-held, temperature compensated refractometers, are incorporated herein by reference.

Figure 3:
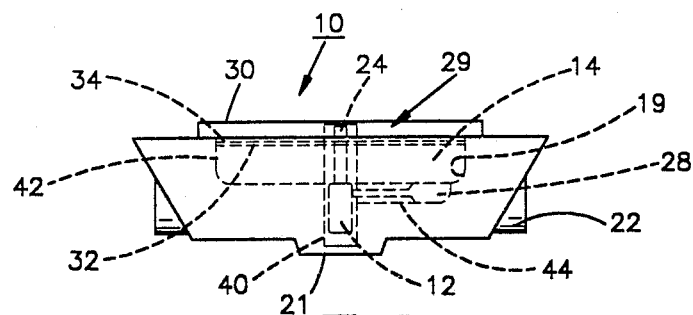
FIG. 3 is an end view of the illuminator of the present invention taken along the line 3—3 of FIG. 2.
Figure 4:
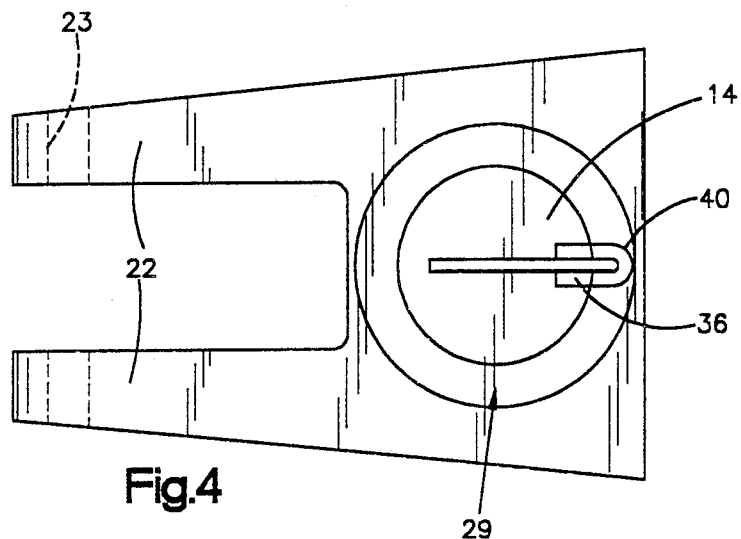
FIG. 4 is an enlarged top view of the illuminator of the present invention as shown in FIG. 1.

In the embodiment of the illuminator shown, the illuminator assembly 18 comprises the light source, power source, operating assembly, and an internal cavity 19 in the cover plate 11 supporting the assembly. The internal cavity 19, as specifically illustrated in FIGS. 2, 3 and 5, includes portions for supporting elements of the light source, power source and operating assembly. The light source 12 is housed within an internal cavity portion, in the form of a substantially cylindrical tube cavity 40 having a central axis transverse to the main prism surface 20. A portion 42 of the internal cavity is also configured for accommodating the power source 14. Similarly, the operating assembly is supported in the internal cavity in groove-like portions 44 configured for accommodating elements of the operating assembly 16.

The removable cover plate 11 is further comprised of a light transmitting material, and includes a substance engaging surface 21 and leg portions 22 having apertures 23 therethrough for removable hinged engagement with the refractometer body B by a pivot pin 23a.

The light source 12 is positioned in the cover plate internal cavity 19 on or about the main prism surface 20 of the prism assembly B, illuminate the fluid substance C supported thereon for measurement. The tube cavity 40 housing the light source enables the fluid substance C to be illuminated at an angle α with respect to the main prism surface 20. The light source may be provided by a conventional and commercially available light emitting diode (LED), as shown schematically in FIGS. 2, 3 and 5. The LED is of a sufficient voltage to adequately illuminate the liquid to be measured, without rapidly depleting the power source during the measuring operations.

The power source 14 operating the light source is provided by a conventional and commercially available miniature battery, such as a three volt lithium based battery. The power source 14 illustrated in FIGS. 1–4 is of a sufficiently small size to be conveniently housed within the cover F or, alternately, within the refractometer body B.

The operating assembly 16 for manually activating the light source is used by selectively bringing elements of the assembly into communication with the power source. The operating assembly, like the power source, could also be provided either internally or externally on or about the refractometer body.

The operating assembly illustrated in FIGS. 2–5, includes a finger operated switch comprising a cap 29 covering a first contact element or wire 24 positioned for engagement with the battery at a negative terminal and with the light source 12, a second contact element 26 engaging the battery at a positive terminal, and a resistor 28 for limiting current flow to the light source and interconnected between the battery and the light source 12 via the first contact element 24. A cover 36, such as flexible tape, is used to isolate terminal surfaces of the battery to prevent inadvertent contact between the battery and first and second contacts 24, 26 operating the light from the contact elements, and thus prevent inadvertent contact between the battery and contact elements 24, 26 operating the light source.

The cap 29 includes an external surface 30 for applying pressure to activate the light source, and an internal surface 32 for engagement with the first contact 24 upon the application of such pressure. A seat 34 extends from the internal surface 32 for maintaining the cap 29 on the cover in press-fit engagement with the portion 42 of the internal cavity 19 housing the battery.

The operating assembly is activated as necessary by manually providing pressure to the external cap surface 30 in the direction of the arrow illustrated in FIG. 2. Upon the application of sufficient pressure, the internal surface 32 engages the first contact 24 and further biases the contact into engagement with the battery, thereby completing the circuit and activating the light source. Additionally, the fluid substance C applied to prism surface 20 for testing also receives the pressure applied to the cover plate 11. The substance C is thus forced into contact with the engagement surface on the cover plate, such that a thin sample of the substance is illuminated during testing. The light source is deactivated once pressure is removed from the cap 29 to disengage the switch from the battery and break the circuit.

Figure 5:
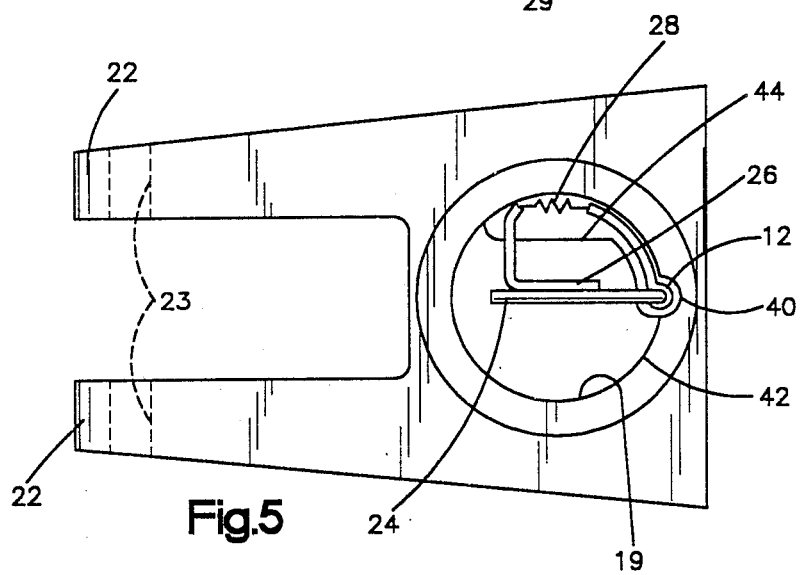
FIG. 5 is an enlarged top view of the illuminator of the present invention with a portion of the device removed to more clearly illustrate a portion of the internal operations.

As illustrated in FIG. 5 with the battery removed, the first and second contacts 24 and 26 comprise contact wires for engagement with the battery to complete the illuminator circuit and activate the light source. The second element 26, as illustrated in FIG. 2, is positioned to continuously engage the battery, while the first contact 24 is spaced from the battery until pressure is applied as described above. The resistor 28 is of a conventional and commercially available type, and of sufficient ohmic value, such as 500Ω, to obtain the desired level of illumination from the light source, without excessively reducing the life of the battery during measurement operations. While examples of compatible levels of power output, light emission, and ohmic resistance are provided herein, other desired combinations are readily obtainable.

By using the invention as illustrated, an operator measuring the concentration of a substance using a refractometer is able to conveniently use an illuminator mounted on the refractometer in an unlighted or dimly lighted area. Further, use of the illuminator does not inhibit normal usage in daylight or artificial light, and may also be used to argument available light. If parts of the illuminator become inoperative, the entire illuminator is capable of being removed and disposed of. Further, if individual parts of the illuminator invention require replacement due to wear, for example the power source, these may also be replaced.

While a preferred embodiment of the invention has been disclosed in detail, the present invention is not to be considered limited to the precise constructions disclosed herein. Various adaptations, modifications and uses of the invention may occur to those skilled in the art to which the invention relates and the intention is to cover all such adaptations, modifications and uses falling within the spirit or scope of the appended claims.

I claim:

1. An illuminator for use in a refractometer having a body housing a prism assembly and measuring assembly for measuring the composition and density of a substance, said illuminator comprising,
   (a) a light source;
   (b) a power source for operating the light source;
   (c) operating means for selectively activating the light source;
   (d) said light source, power source and operating means together defining an illuminator assembly for supporting the light source in a position on or about said prism assembly to illuminate a fluid substance to be measured; and,
   (e) said illuminator assembly being housed in a cover removably mounted on the refractometer body and on or about said prism assembly.

2. The illuminator of claim 1 wherein the cover is of a light transmitting material and is hinged to the refractometer for engagement with a substance to be measured.

3. The illuminator of claim 2 wherein the cover housing the illuminator assembly includes an internal cavity supporting the light source at an angle transverse to a main prism surface of a prism assembly, and a cap is press-fit into engagement with the cover to maintain the illuminator assembly within the cavity.

4. The illuminator of claim 1 wherein the light source comprises a light emitting diode, and the power source comprises a battery.

5. In a refractometer for measuring the composition of substances comprising a hand-held refractometer body which mounts a prism and a measuring assembly having a prism surface for supporting a fluid substance to be measured, and an illuminator for illuminating the fluid substance to be measured, the illuminator comprising,
   (a) an illuminator assembly including a light source, power source, and operating means for manually activating the light source by energizing said power source;
   (b) said light source, power source and operating means being mounted in a cover which is pivotally and detachably connected to said refractometer body for supporting said light source in a position on or about said prism surface to illuminate and/or pass light through a substance to be measured.

6. The illuminator in accordance with claim 5 wherein said cover is made from a light transmitting material and has a cavity formed therein to receive said illuminator assembly therein.

7. The illuminator of claim 6, wherein said cavity formed in said cover supports said light source at an angle transverse to a main prism surface of said prism.

8. The illuminator of claim 6, wherein said cover is pivotally connected to said refractometer body so as to pivot about an axis which is perpendicular to the longitudinal central axis of said refractometer thereby to be pivoted toward and away from said prism surface and to be disposed in generally parallel alignment with said prism surface.

9. The illuminator of claim 5, including a resistor means in circuit with said operating means and said power source for controlling the illumination from said light source.

* * * * *